United States Patent
Feldman et al.

[11] Patent Number: 5,254,004
[45] Date of Patent: Oct. 19, 1993

[54] SELF-TIGHTENING CHUCK FOR DENTAL TOOLS

[75] Inventors: Michael Feldman, Howell; Moshe Meller, Princeton, both of N.J.

[73] Assignee: Erah Meller, Haifa, Israel

[21] Appl. No.: 7,244

[22] Filed: Jan. 21, 1993

[51] Int. Cl.⁵ .................................................. A61C 1/14
[52] U.S. Cl. ..................................................... 433/129
[58] Field of Search ........................ 433/126, 127, 129; 279/2.04, 144

[56] References Cited
U.S. PATENT DOCUMENTS 3,960,039  6/1976  Nash et al. .......................... 433/126
3,973,784  8/1976  Smith ................................. 279/144

Primary Examiner—John J. Wilson
Attorney, Agent, or Firm—Frishauf, Holtz, Goodman & Woodward

[57] ABSTRACT

A rotary dental drive tool has a rotatable driving member which is connected to a working tool via a self-tightening chuck, the rotatable driving member rotating in a clockwise direction during use. The chuck includes a chuck member having a tool-engaging internal surface portion for receiving a working tool therein, the chuck member having a tapered outer surface portion which is engageable with a tapered inner surface portion of the rotatable driving member so as to press the tool-engaging internal surface portion of the chuck member against the working tool to fixedly engage the working tool with said rotatable driving member via the chuck member. The chuck member has a left-hand threaded screw member on an outer surface portion thereof, which is engageable with a left-hand threaded screw portion on an inner surface portion of the rotatable driving member. The chuck member is rotatable in a left-hand threaded manner into the screw threaded portion of the rotatable driving member so as to cause the tapered surfaces to mutually engage and press the tool-engaging surface portion of the chuck member against the working tool responsive to rotation of the rotatable driving member, whereby the chuck member automatically self-tightens against the working tool during operation of the dental drive tool, and the working tool rotates with the rotatable driving member.

16 Claims, 2 Drawing Sheets

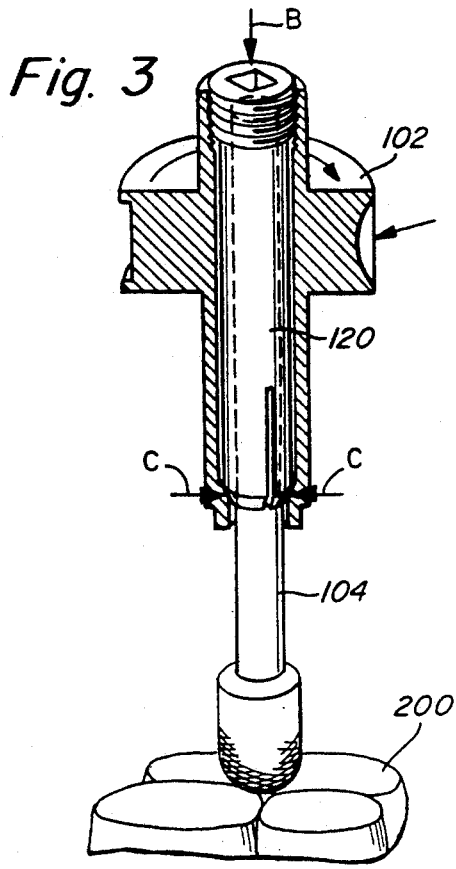
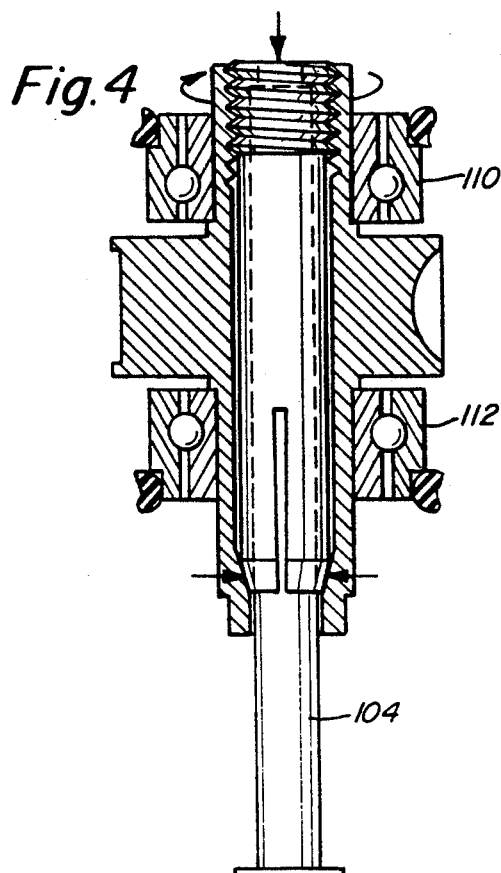
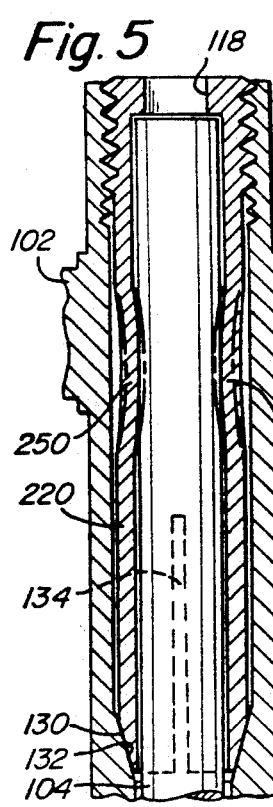
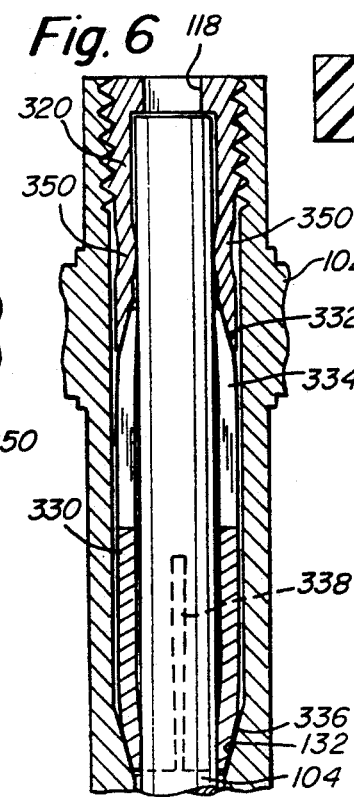
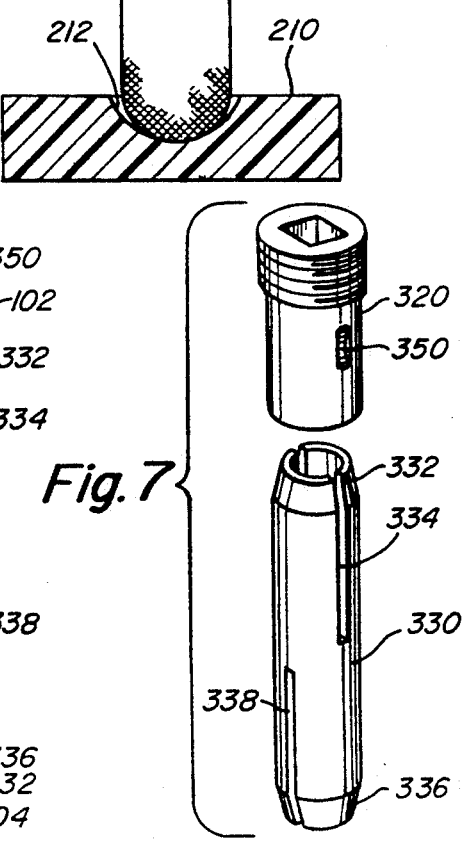

SELF-TIGHTENING CHUCK FOR DENTAL TOOLS

BACKGROUND OF THE INVENTION

This invention relates to high speed dental drill-type tools, and more particularly to a high speed dental drill-type tool having a self-tightening chuck, which self-tightens during operational use of the dental drill-type tool, and which eliminates the necessity for very strong or powerful manual pre-tightening of the chuck holding the working tool before beginning a dental operation.

In the prior art, when practitioners use a dental drill-type tool (hereafter referred to as a dental drill) providing rotary drive to a working tool, such as a drill bit, the working tool is coupled to the rotary drive or turbine member of the drill by means of a chuck which is tightened manually before use. Thus, an extra operation of tightening the chuck with a small tightening tool, which is easily misplaced, is required. Moreover, if the chuck in the prior art is inadvertently not tightened before use, or is not tightened sufficiently (i.e., the tightening force is not strong or powerful enough), there is a possibility of the tool flying out of the drill during start-up or during operation, thereby creating a danger to the patient and/or to the practitioner, and possibly causing damage to the drill mechanism or other nearby objects.

Still further, in the prior art dental drill tools, when the tool is operated in the mouth of a patient, if too much force is applied to the working tool during use, for example by pressing too hard on a tooth or mouth structure of the patient, the rotation of the turbine of the drill tends to be slowed down, and the reaction forces are such as to loosen the conventionally-used right-hand threaded tool holding chucks, thereby creating a danger that the tool may fly out of the chuck and injure the patient, or that the upper screw-threaded member of the conventional chuck (see FIG. 2) may unthread and move upwardly in the direction of arrow A (FIG. 2) within the drill housing and jam against an upper cover thereof, thereby damaging the internal mechanism of the dental drive tool.

The object of the present invention is to provide a dental drill drive tool having a self-tightening chuck which is easy to use, which is self-tightening at the beginning of use, which self-tightens during use, and which eliminates the disadvantages of the prior art chuck mentioned above.

SUMMARY OF THE INVENTION

According to the present invention, a rotary dental drive tool has a rotatable driving member which is connected to a working tool via a chuck arrangement, the rotatable driving member rotating in a clockwise direction during use. The improved chuck arrangement of the present invention comprises a chuck member having a tool-engaging internal surface portion for receiving a working tool therein, the chuck member having a tapered outer surface portion, the tapered outer surface portion being engageable with a tapered inner surface portion of the rotatable driving member so as to press the tool-engaging internal surface portion of the chuck member against the working tool to fixedly engage the working tool with the rotatable driving member via the chuck member. A left-hand threaded screw member is provided on an outer surface portion of the chuck member and which is engageable with a left-hand threaded screw portion of on an inner surface portion the rotatable driving member, the chuck member being rotatable in a left-hand threaded manner into the screw threaded portion of the rotatable driving member so as to cause the tapered surfaces to mutually engage and press the tool-engaging surface portion of the chuck member against the working tool responsive to rotation of the rotatable driving member, whereby the chuck member automatically tightens against the working tool during operation of the dental drive tool to thereby cause the working tool to rotate with the rotatable driving member.

According to a further optional feature of the invention, the chuck member further comprises engaging means for lightly frictionally engaging the working tool prior to pressing of the tool-engaging surface portion of the chuck member against the working tool, whereby when the rotatable driving member is initially caused to rotate to produce a working tool-driving force, the rotatable driving member rotates in an opposite rotational direction relative to the working tool to cause threaded rotational engagement of the left-hand threaded screw members to cause positive engagement of the tapered surfaces and automatic tightening of the chuck member against the working tool.

A method of tightening a chuck of a dental drill to a working tool, comprises providing a dental drill having a rotatable drive member with a chuck member threadably coupled to the rotatable drive member, the threaded coupling between the rotatable drive member and the chuck member being a left-hand threaded engagement wherein the rotatable drive member rotates in a clockwise direction during use; inserting a working tool into the chuck member; and turning on the dental drill and pressing the inserted working tool against a surface to cause reaction forces such that the chuck member automatically threads into the rotating rotatable drive member in a self-tightening direction during operation of the dental drill.

BRIEF DESCRIPTION OF THE DRAWINGS

FIG. 3 shows a portion of the chuck of FIG. 1, partly in section, so as to more clearly illustrate the present inventive concept;

FIG. 4 is another partial view of the chuck and drive tool arrangement of the present invention, showing a method of self-tightening thereof;

FIG. 5 illustrates a modification of the present invention, in cross section, wherein engaging means is provided for engaging the chuck with the working tool during the self-tightening operation;

FIG. 6 is a another sectional view showing another modified embodiment of the present invention with engaging means for engaging the working tool during self-tightening thereof; and FIG. 7 is a perspective view of the internal chuck member of the embodiment of FIG. 6, more clearly showing the construction of the two-piece internal self-tightening chuck member of FIG. 6.

DETAILED DESCRIPTION

The self-tightening chuck of the present invention is useful in substantially any type of dental drill-type tools, for example the type driven by pressure air and having a turbine-type drive mechanism. Such a dental drill drive tool is illustrated in U.S. patent application Ser. No. 08/002,350, filed Jan. 13, 1993, the entire contents of which are incorporated herein by reference.

Figure 1:
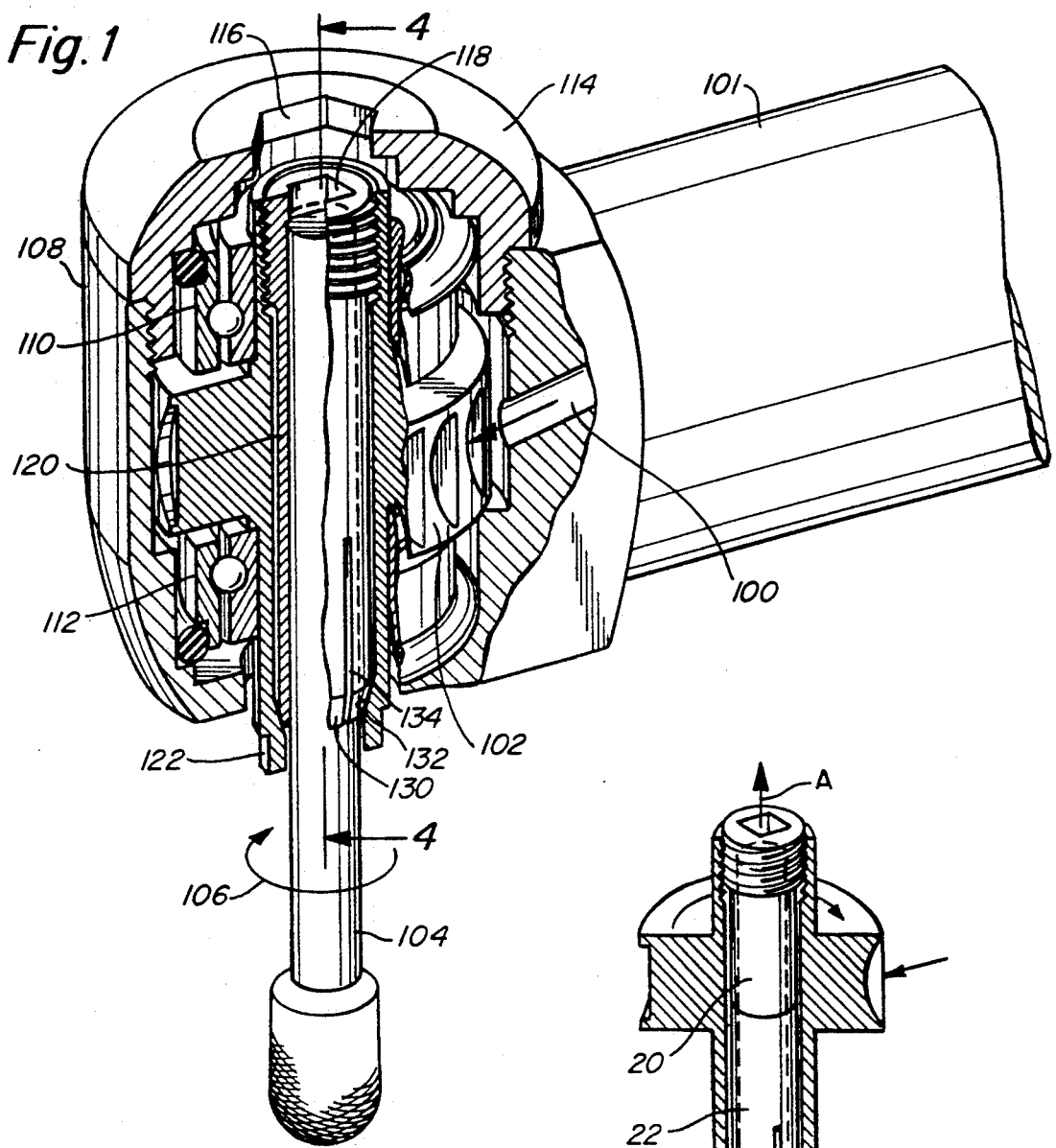
FIG. 1 is a shows a portion of a dental drill for driving a working tool, shown partly in section, illustrating the left-hand threaded self-tightening chuck arrangement of the present invention.

Referring to FIG. 1, showing only the relevant parts of a dental drive tool (drill), a dental drive tool (drill) comprises a conduit 100 extending through a handle portion 101 for supplying drive air (compressed air) against the vanes of a rotatable turbine member 102 to cause driving of the working tool 104 in the direction of the arrow 106. The turbine member 102 is supported in the head portion 108 of the drill housing by means of bearings 110, 112. The construction of the housing 108 and internal mechanism and operation of the rotatable turbine member 102 and the support structure therefor, is known and is described in said above-identified co-pending application Ser. No. 08/002,350, the entire contents of which are incorporated herein by reference. The turbine member 102 has an elongated vertically extending opening in the center thereof, in which is received a chuck member 120 which receives therein an elongated shaft of a working tool 104, in order to rotatably "lock" or "couple" the shaft of the working tool 104 with the turbine member 102 when the chuck member 120 is tightened.

The head portion 108 of the drill housing has a screw-on cap member 114 which has an access opening 116 in the central portion thereof within which to insert a conventional-type of tightening square-ended tool (not shown) to engage with the square opening or recess 118 in the upper end of the chuck member 120. The lower end of the turbine member 102 has a projecting square-profile portion 122 (or other tightening-tool-engaging profile) for engaging a tightening tool (or for being grabbed by fingers of the practitioner to hold same stationary) so that the upper end of the chuck member can be at least partly tightened relative to the turbine member 102 by screwing in the chuck member 120 relative to the turbine member 102. Thus, for manual tightening of the chuck, a tightening tool member is engaged at portion 122 and another tightening tool member is engaged in the opening 118 of the chuck member 120. Then, portions 122 and 118 are rotated relative to each other to tighten the members 120, 108 relative to each other to cause an outer tapered engaging surface 130 of the chuck member 120 to engage an inner tapered surface 132 of the turbine member 102, such that the tapered surface portions 130 of the chuck member 120 are pressed inwardly by the tapered surface portions 132 of the turbine member 102 to tighten against the outer surface of the working tool 104. In the conventional chucks, which tend to loosen during use if sufficient pressure is placed upon the working tool, it was necessary to manually tighten the chuck with a very high or strong tightening force. In the present invention, on the other hand, since, upon use of the tool, the chuck self-tightens, is only desirable to manually pre-tighten the chuck to a small degree, or to manually pre-tighten the chuck to a much lesser degree of tightness than is required in the prior art devices. In the embodiment shown in FIG. 1, wherein the upper portion of the chuck member 120 and the turbine member 102 have left-hand threaded screw portions, the chuck member 120 is rotated counterclockwise relative to the turbine member, to tighten the chuck.

Figure 2:
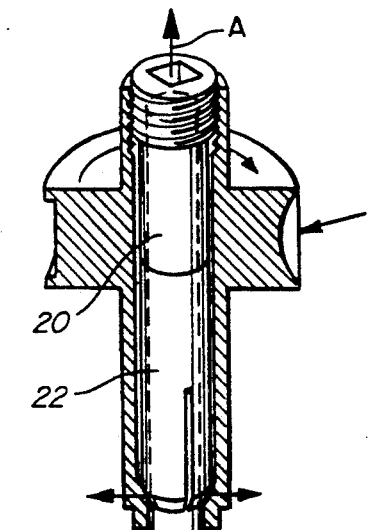
FIG. 2 shows a prior art chuck.

Conventional dental drills rotate in a clockwise direction when viewed from the top, as shown for example in FIGS. 1 and 2 of the drawings. This is an international standard of operation for dental drills, and all available dental drill burs and other dental working tools have cutting surfaces which are specifically designed to operate in connection with dental drills which rotate in the clockwise direction as shown in FIGS. 1 and 2 of the drawings. Therefore, throughout the description, this convention is adhered and it should be clear that, if rotation in the opposite direction is desired, then the chuck must be threaded with a thread direction opposite to the direction of rotation of the rotating turbine member of the dental drill.

As is conventional, the chuck member 120 has longitudinal slits 134 in the lower tapered portion thereof to provide resilient segments thereof at the lowered tapered portions to facilitate tightening of the tapered portion against the shaft of the working tool 104 when the chuck is tightened. The feature of the slits and the resilient elongated segments at the lower portion of the chuck is conventional, as is shown in FIG. 2. What is not conventional, however, is the provision of the left-hand threaded screw portions at the upper portion of the chuck 120 and the turbine member 102 which has the improved effects which are discussed hereinbelow.

The improvement of the present invention, having the left-hand threaded screw portions for engaging the chuck 120 with the working tool 104, is that when the drill is first turned on after insertion of the working tool 104 into the head end of the drill, and without requiring strong or powerful manual pre-tightening of the chuck, the reaction forces due to the inertia of the working tool 104 and the initial spinning of turbine member 102, are such as to cause the chuck to self-tighten on the shaft of the working tool 104. Light manual pre-tightening before use is desired, but is not absolutely required. This self-tightening effect is caused by the internal friction forces and inertia forces when the drill is first turned on. Then, when the working end of the working tool 104 is pressed against a tooth or other structure in the mouth, or against some other surface, the rotating force of the turbine member 102 and the reaction force of the working tool 104 against the surface against which it is placed, are such that the chuck will automatically self-tighten, thereby further tightening the engagement of the working tool with the drill turbine member 102, further enhancing safety in use. In use, even if the working tool 104 is pressed very hard against a tooth or other structural surface in the mouth of a patient, the reaction forces are such as to thereby cause tightening of the chuck, rather than loosening of the chuck as occurs in the prior art. FIG. 3 of the drawings shows the self-tightening effect while the turbine member 102 is rotated in the direction of the arrow, and the working tool 104 is placed against the surface of a tooth 200, to cause reaction forces to thread the chuck member 120 into the turbine member 102 in the direction of the arrow B in FIG. 3, to cause tightening of the tapered surface portions of the chuck against the shaft of the working tool, as indicated by the arrows C in FIG. 3.

In the above discussion, and in the following discussions, the term "left-hand threaded" is used in connection with describing the engaging screw threads of the chuck member and of the rotatable turbine member. This is because in the arrangement of the present invention, and in all currently available dental drills, the turbine member rotates in a clockwise direction, as viewed from the top, and as indicated by the arrows in FIGS. 1 and 2. For such clockwise rotation of the turbine member, the left-hand threaded screw arrangement of the present invention is advantageous to produce the desired effects discussed above. As mentioned hereinabove, the international standard for dental drills is the above-described clockwise rotation of the turbine member, and all tools are made according to such international standard with cutting angles adapted for operation in a clockwise rotational direction. If, on the other hand, the turbine member is rotated in a counterclockwise direction (opposite to the direction shown in the drawings of the present application) then an oppositely threaded right-hand threaded screw arrangement should be used to achieve the effects of the present invention.

FIG. 4 illustrates the arrangement of FIG. 3 in an enlarged form and in somewhat greater detail, but with the working end of the working tool 104 placed against a tightening block 210 having a cavity 212 therein. In order to self-tighten the chuck against the shaft of the working tool 104, the drill is turned on (i.e., after optionally manual light pre-tightening of the chuck), and the working tool 104 is pressed into the cavity 212 of the elastomeric tightening block 210 to create additional reaction forces which result in tightening of the chuck as discussed hereinabove with respect to FIG. 3. The tightening block 210 is made of a tough elastomeric material such as hard rubber or hard synthetic rubber, so as not to damage the working end of the working tool 104, while also providing a long life for the tightening block 210.

The chuck members described above are all one-piece chuck members which are generally conventional except for the provision of the left-hand threaded engaging screw portions at the upper end thereof. FIG. 5 shows a modified one-piece chuck member of the present invention having an additional working tool engaging portion which increases the frictional forces between the chuck member and the working tool so as to enhance the self-tightening effect. In FIG. 5, the same reference numerals are used for elements corresponding to the previously described elements.

Referring to FIG. 5, the turbine member 102 is substantially the same as the turbine member 102 described hereinabove with respect to FIGS. 1-4. The chuck member 220 has a lower portion having longitudinal slits 134 therein (the same as previously described), the outer surface of the lower portion of the chuck member 220 having outer tapered surfaces 130 which engage against inner tapered surfaces 132 of turbine member 102. The upper threaded portion of the chuck member 220 and the upper threaded portion of the turbine member of FIG. 5 are the same as previously described with respect to FIGS. 1, 3 and 4.

As shown in FIG. 5, according to another embodiment of the invention, the chuck member 220 has resilient partially cut-out portions or depression portions 250 (see FIG. 7 for an illustration of typical depression portions 250). The resilient depression portions 250 protrude inwardly of the chuck member 220. When the shaft of the working tool 104 is inserted into the interior of the chuck member 220, the upper portions of the shaft press against the inwardly protruding depression portions 250 in a frictional manner and flex the inwardly directed depression portions 250 outwardly from the dashed line positions to the solid line positions as shown in FIG. 5. Thus, upon insertion of the working tool, the chuck member 220 is resiliently and frictionally engaged with the shaft of the working tool 104, as shown in FIG. 5. This enhances the self-tightening effect of the present invention, particularly during initial turn-on of the dental drill, as is described below.

When the working tool is inserted into the chuck member 220 of FIG. 5, and the drill is turned on, the inertia of the tool 104 and of the resiliently frictionally engaged chuck member 220 tend to cause same to remain stationary. When turbine member 102 is rotated against the inertia of the working tool 104 and chuck member 220, the upper left-hand threaded portion of the chuck member is caused to thread inwardly into the left-hand threads of the turbine member 102 to cause the chuck member 220 to move downwardly in the turbine member 102 to cause the outer tapered surfaces 130 to press against the inner tapered surfaces 132 of the turbine member 102 to press the lower tapered portion of the chuck member 220 against the shaft of the working tool 104, thereby self-tightening the chuck apparatus. If desired, the chuck could be manually pre-tightened before turn on of the dental drill, as described hereinabove. Thereafter, if desired, the working end of the working tool can be placed against a tightening block 210 (as shown in FIG. 4) to further increase the tightening of the chuck, or the practitioner can immediately begin working in the mouth of the patient (as shown in FIG. 3) which will also cause self-tightening of the chuck during operation. As mentioned above, since the opening 118 is provided, the chuck may be manually lightly tightened or fully tightened before use, if desired. As also mentioned above, when the device is used in the mouth, and if the pressure against a tooth or other surface is increased, instead of providing a tendency of loosening of the chuck as in the prior art, the apparatus of the present invention tends to tighten the chuck, thereby providing a self-tightening effect and improving safety.

Other types of frictional engaging members on the inner surface of the chuck member could be provided. For example, a sleeve could be inserted inside the chuck member, the sleeve having inwardly bent resilient portions, or an elastomeric material can be provided in the interior of the chuck member to provide the additional frictional forces with the shaft of the working tool 104. The frictional engagement should be such as not to impede insertion of the shaft of the working tool 104 into the chuck member.

The arrangement of FIG. 5 is particularly advantageous for use in connection with the elastomeric tightening block 210 shown in FIG. 4. The practitioner need merely to insert the working tool into the chuck, and to turn on the drill and press the working end of the working tool 104 against the elastomeric block 210. Even if the inertia effects are insufficient to cause tightening, the combination of use of the elastomeric tightening block 210 and the resilient inwardly bent portions 250 will combine to provide even better total self-tightening, without the use of any tools whatsoever. FIG. 5 shows the jaws of the chuck in the not-yet tightened position. Upon rotation of the turbine member 102, the chuck member 220 is screwed downwardly in the turbine member 102 to cause self-tightening (as shown in FIG. 6).

In the prior art, as shown in FIG. 2, it was attempted to use a two-piece chuck structure (members 20 and 22 in FIG. 2). It was believed that such a two-piece chuck structure would help prevent self-loosening of the chuck if too much pressure was applied at the working end of the working tool 104. The thought was that if too much pressure is applied, instead of loosening the chuck, slippage would occur at the junction between the chuck members 20, 22 to prevent loosening. However, this was not an effective solution and did not overcome the problems of the prior art which are overcome by the device of the present invention. In the prior art device, the frictional forces at the interface between the upper and lower chuck members 20, 22 was still sufficient to transmit enough force to cause undesired disengagement of the chuck if too much force is applied to the working end of the working tool 104. The inadvertent releasing of the chuck under such conditions is overcome by the apparatus of the present invention.

FIG. 6 shows another embodiment of the present invention utilizing a two-piece chuck member. In FIG. 6, the chuck member comprises an upper portion 320 having the left-hand threaded screw portion thereon which engages with the internal left-hand threaded screw portion of the turbine member 102. The upper portion 320 of the chuck member (also shown in FIG. 7) has dimples or inwardly bent portions 350 which frictionally and resiliently engage the shaft of the working tool 104 inserted therein, as shown in FIG. 6. The lower portion 330 of the chuck member has an upper tapered portion 332 (FIG. 7) and longitudinal slits 334 therein. The lower portion of the lower chuck member 330 has outer tapered surface portions 336 and longitudinal slits 338 therein. In use, the dimples or inwardly bent portions 350 frictionally engage (preferably light frictional engagement) the upper portion of the shaft of the working tool 104 inserted therein. Upon rotation of the turbine member 102, the chuck is self-tightening as described above. Screwing of the upper chuck portion 320 into the rotating turbine member 102 causes the upper chuck portion 320 to move downwardly in the turbine member 102 to press the upper chuck member 320 downwardly against the lower chuck member 330. This causes locking of the lower chuck member 330 to the shaft of the working tool 104 at the upper tapered portions 332 as well as at the lowered tapered portions 336, as clearly seen in FIGS. 6 and 7.

As should be clear, the "grabbing dimples" 350 which frictionally engage the outer surface of the shaft of the working tool 104 can be provided or not, as desired. Moreover, the "grabbing dimples" 350 can be replaced with the inwardly bent resilient portions 250 of FIG. 5.

The embodiment of FIGS. 6 and 7 is particularly advantageous since it increases the tightening effect and improves the tightening integrity of the overall structure. However, the two-piece chuck structure of FIGS. 6 and 7 is more expensive than the one-piece chuck structures of FIGS. 1, 3, 4 and 5, which provide sufficient self-tightening effects. As should be clear, the optional embodiments of FIGS. 5-7, wherein frictional engagement with the shaft of the working tool 104 is provided relative to the chuck member, are particularly advantageous since the operator can merely insert the working tool 104 into the chuck, without any tightening at all (although light manual pre-tightening is preferred). Then, when the device is first used on a tooth or the like, the reaction forces against the tooth (or against an elastomeric tightening block 210 of FIG. 4) will cause full self-tightening of the chuck immediately when the turbine is turned on to rotate the turbine member 102.

While the invention has been described above with respect to specific features, it is clear that various modifications and alterations can be provided within the scope of the appended claims, and it is also clear that features of the various embodiments can be combined and interchanged, as desired, within the scope of the appended claims.

What is claimed is:

1. In a rotary dental drive tool having a rotatable driving member which is connected to a working tool via a chuck arrangement, the rotatable driving member rotating in a clockwise direction during use, the improvement wherein the chuck arrangement comprises:
   a chuck member having a tool-engaging internal surface portion for receiving a working tool therein, said chuck member having a tapered outer surface portion, said tapered outer surface portion being engageable with a tapered inner surface portion of said rotatable driving member so as to press said tool-engaging internal surface portion of said chuck member against said working tool to fixedly engage said working tool with said rotatable driving member via said chuck member; and
   a left-hand threaded screw member on an outer surface portion of said chuck member and which is engageable with a left-hand threaded screw portion on an inner surface portion of said rotatable driving member, said chuck member being rotatable in a left-hand threaded manner into said screw threaded portion of said rotatable driving member so as to cause said tapered surfaces to mutually engage and press said tool-engaging surface portion of said chuck member against said working tool responsive to rotation of said rotatable driving member, whereby said chuck member automatically tightens against said working tool during operation of the rotary dental drive tool and said working tool rotates with said rotatable driving member.

2. The rotary dental drive tool of claim 1, wherein said chuck member further comprises engaging means for lightly frictionally engaging said working tool prior to pressing of said tool-engaging surface portion of said chuck member against said working tool, whereby when said rotatable driving member is initially caused to rotate to produce a working tool-driving force, said rotatable driving member rotates in an opposite rotational direction relative to said working tool to cause threaded rotational engagement of said left-hand threaded screw members to cause positive engagement of said tapered surfaces and tightening of said chuck member against said working tool.

3. The rotary dental drive tool of claim 1, wherein said chuck member comprises an elongated generally cylindrical member having said left-hand threaded screw portion at an upper surface portion thereof, and having said tool-engaging internal surface portion and said tapered outer surface portion at a lower portion thereof.

4. The rotary dental drive tool of claim 3, wherein said generally cylindrical member has longitudinal slits formed at spaced portions around the periphery thereof for increasing resiliency of the lower portion thereof.

5. The rotary dental drive tool of claim 1, wherein said upper portion of said chuck member has a tool engaging means for receiving a tightening tool for manually tightening said chuck member against said working tool.

6. The rotary dental drive tool of claim 1, wherein said chuck member comprises an elongated generally cylindrical member, and further comprises resilient engaging means resiliently projecting inwardly from the internal surface of said generally cylindrical member for resiliently frictionally engaging a working tool inserted into said chuck member.

7. The rotary dental drive tool of claim 6, wherein said resilient engaging means comprises partially cutout portions of said generally cylindrical member which resiliently project inwardly of said generally cylindrical member.

8. The rotary dental drive tool of claim 1, wherein said chuck member comprises a one-piece elongated cylindrical member.

9. The rotary dental drive tool of claim 1, wherein said chuck member comprises a two-piece elongated cylindrical member.

10. The rotary dental drive tool of claim 9, wherein said chuck member comprises upper and lower cylindrical members, said upper and lower cylindrical members having mutually engaging tapered surface portions for frictionally engaging said working tool during tightening of said chuck member.

11. The rotary dental drive tool of claim 9, wherein one piece of said two piece chuck member has said screw threaded portion thereon, and wherein said one piece comprises means projecting internally of said chuck member for frictionally engaging a surface of said working tool which is inserted in said chuck member.

12. The rotary dental drive tool of claim 1, further comprising means projecting inwardly of said chuck member, into a space into which said working tool is insertable, for frictionally engaging a portion of a working tool inserted in said chuck member to improve automatic self-tightening of said chuck member against said working tool.

13. The rotary dental drive tool of claim 1, further comprising a tightening block member made of resilient material against which said working tool is contactable for tightening said chuck member upon rotation of said rotatable driving member and upon contacting of said working tool with said tightening block member.

14. A method of tightening a chuck of a dental drill to a working tool, comprising:
providing a dental drill having a rotatable drive member with a chuck member threadably coupled to the rotatable drive member, the threaded coupling between the rotatable drive member and the chuck member being a left-hand threaded engagement wherein the rotatable drive member rotates in a clockwise direction during use;
inserting a working tool into the chuck member; and
turning on said dental drill and pressing the inserted working tool against a surface to cause reaction forces such that the chuck member automatically threads into the rotating rotatable drive member in a self-tightening direction during operation of the dental drill.

15. The method of claim 14, further comprising manually tightening said chuck member into said rotatable drive member, before turning on said dental drill, by manually rotating said chuck member relative to said rotatable drive member in a counterclockwise direction, and then turning on said dental drill to further tighten said chuck member.

16. The method of claim 14, wherein said chuck member includes resilient engaging means for lightly resiliently engaging said working tool when inserted in said chuck member, prior to turning on of said dental drill and prior to tightening of said chuck member.

* * * * *

UNITED STATES PATENT AND TRADEMARK OFFICE
CERTIFICATE OF CORRECTION

PATENT NO. : 5,254,004
DATED : October 19, 1993
INVENTOR(S) : FELDMAN, Mike et al It is certified that error appears in the above-indentified patent and that said Letters Patent is hereby corrected as shown below:

Title page, Section [73] Assignee,

"Erah" should be --Eran--.

Signed and Sealed this

Twenty-first Day of June, 1994

Attest:

BRUCE LEHMAN

Attesting Officer    Commissioner of Patents and Trademarks